United States Patent [19]

Petschow

[11] Patent Number: 5,660,842

[45] Date of Patent: Aug. 26, 1997

[54] INHIBITION OF HELICOBACTER

[75] Inventor: Bryon W. Petschow, Evansville, Ind.

[73] Assignee: Bristol-Myers Squibb Company, Princeton, N.J.

[21] Appl. No.: 435,566

[22] Filed: May 5, 1995

Related U.S. Application Data

[63] Continuation-in-part of Ser. No. 317,441, Oct. 4, 1994, abandoned.

[51] Int. Cl.$^6$ ..................................................... A61K 9/36
[52] U.S. Cl. ........................... 424/405; 424/450; 424/440; 424/441; 424/451; 424/464
[58] Field of Search .................................. 424/450, 458, 424/405, 442; 514/2

[56] References Cited

U.S. PATENT DOCUMENTS

| | | | |
|---|---|---|---|
| 5,304,540 | 4/1994 | Blackburn et al. | 514/2 |
| 5,504,072 | 4/1996 | Schmidl et al. | 514/2 |

FOREIGN PATENT DOCUMENTS

| | | | |
|---|---|---|---|
| 0465423A2 | 6/1990 | European Pat. Off. | 31/19 |

*Primary Examiner*—Thurman K. Page
*Assistant Examiner*—D. Faulkner
*Attorney, Agent, or Firm*—Thomas R. Savitsky

[57] ABSTRACT

The present invention is directed to a method for inhibiting Helicobacter by administering $C_8$–$C_{16}$ monoglycerides of fatty acids or lauric acid. The monoglycerides and/or lauric acid are conveniently administered via a nutritional composition.

35 Claims, 1 Drawing Sheet

INHIBITION OF HELICOBACTER

CROSS REFERENCE TO RELATED APPLICATION

This application is a continuation-in-part of application Ser. No. 08/317,441 filed Oct. 4, 1994 (abandoned Feb. 12, 1997).

FIELD OF THE INVENTION

The present invention concerns a method for inhibiting Helicobacter by administration of monoglycerides of $C_8$–$C_{16}$ fatty acids or $C_{12}$ fatty acid, lauric acid.

BACKGROUND OF THE INVENTION

The antimicrobial properties of various free fatty acids and fatty acid esters such as the glycerides have been investigated for many years (Niemans C., Influence of trace amounts of fatty acids on the growth of microorganisms. Bacterial Reviews 1954; 18:147–163 and Kodicek E., The effect of unsaturated fatty acids on gram-positive bacteria. Society for Experimental Biology Symposium 1949; 3: 2180–231). These studies have confirmed that both free fatty acids (FFA) and monoglycerides (MG) are capable of inhibiting the growth of numerous types of bacteria (Kabara J. J., Lipids as host-resistant factors of human milk, Nutr. Reviews 1980; 38: 65–73, Kabara J. J., Fatty acids and derivatives as antimicrobial agents. A review. In: Kabara J. J., ed. The Pharmacological Effect of Lipids. Champaign, IL: American Oil Chemist Society, 1978: 1–14 and Knapp H. R., Melly M. A., Bactericidal effects of polyunsaturated fatty acids. J Infect Dis 1986; 154: 84–94), fungi (Wyss O., Ludwig B. J., Joiner R. R., The fungistatic and fungicidal action of fatty acids and related compounds. Arch Biochem. 1945; 7: 415–425) protozoans (Lees A. M., Korn E. D., Metabolism of unsaturated fatty acids in protozoa. Biochemistry 1966; 1475–1481) and lipid-enveloped viruses (Welsh J. K., Skurrie I. J., May J. T., Use of Semliki Forest virus to identify lipid-mediated antiviral activity and anti-alphavirus immunoglobulin A in human milk. Infect Immun 1978; 19: 395–401). Numerous studies have also described the generation of inhibitory fatty acids or derivatives by the action of lipases on triglycerides in human milk and infant formulas (Isaacs C. E., Kashyap S., Heird W. C., Thormar H., Antiviral and antibacterial lipids in human milk and infant formula feeds. Arch. Dis. Childhood 1990; 65: 861–864; Hernell O., Ward H., Blackberg L., Pereira MEA, Killing of Giardia lamblia by human milk lipases: an effect mediated by lipolysis of milk lipids. J Inf Dis 1986; 153: 715–720). Susceptibility of various bacteria to inactivation by specific fatty acids may be a factor in regulating the different species of bacteria that colonize the various niches in skin as well as the respiratory and gastrointestinal tracts.

Most investigations of the antimicrobial properties of FFA and MG have used in vitro models to evaluate the inhibitory effects of short-chain and long-chain saturated and monounsaturated fatty acids; fewer studies have been done on the inhibitory properties of long-chain polyunsaturated fatty acids. (Kabara J. J., Lipids as host-resistant factors of human milk, Nutr Reviews 1980; 38: 65–73; Kabara J. J., Fatty acids and derivatives as antimicrobial agents. A review. In: Kabara J. J., ed. The pharmacological effect of lipids. Champaign, IL: American Oil Chemist Society, 1978: 1–14 and Knapp H. R., Melly M. A., Bactericidal effects of polyunsaturated fatty acids. J Infect Dis 1986; 154: 84–94; and Thormar H., Isaacs C. E., Brown H. R., Barshatzky M. R., Pessalano T., Inactivation of enveloped viruses and killing of cells by fatty acids and monoglycerides. Antimicr Agents Chemother 1987; 31: 27–31). Results from these studies have led experts to reach the following conclusions with regard to fatty acid structure-activity relationships.

(1) In general, FFA sensitivity is considered to be a characteristic of gram-positive bacteria, with few gram-negative bacteria being sensitive.

(2) Gram-negative bacteria are affected primarily by very short chain FFA (e.g., $C_6$ or less).

(3) Yeasts/fungi are affected by FFA with short chain fatty acids (e.g., $C_{10}$ or less).

For many years the cause of peptic ulcer disease was widely believed to be associated with a disturbance in the balance between the presence of noxious agents found in the stomach and the operation of innate mucosal protective mechanisms. As a result, much of the research on ulcer disease during the past forty years has focused on the role of gastric acid in the genesis of peptic ulceration. While suppression of acid production with histamine 2 (H2)—receptor antagonists is effective in healing acute ulcers, the recurrence rate during the first year can be as high as 90%. This indicates that such treatment is effective in healing the ulcers but not curing the disease.

Few of the early investigations of gastric disease explored an infectious etiology until Marshall and Warren described the isolation of gram-negative spiral-shaped bacteria from biopsy specimens obtained from human subjects with gastritis and peptic ulcers (Marshall B. J., Warren J. R., Unidentified curved bacilli on gastric epithelium in active chronic gastritis. Lancet 1984; i: 1311–1315). These investigators later identified this organism as *Campylobacter pyloridis*. Subsequent studies have confirmed that this bacterium, currently referred to as *Helicobacter pylori*, is a major etiologic agent in chronic diffuse superficial (type B) gastritis and gastroduodenal ulcer disease. Evidence to support such an association is provided by studies in human volunteers that were challenged with *H. pylori* (Marshall B. J., Armstrong J. A., McGeechie D. B., Glancy R. J., Attempts to fulfill Koch's postulates for pyloric Campylobacter. Med. J. Aust. 1985; 142: 436–439 and Morris A., Nicholson G., Ingestion of *Campylobacter pyloridis* causes gastritis and raised fasting gastric pH. Am. J. Gastroenterol 1987;82: 192–199) and the recognition of a similar association between gastric diseases and spiral organisms found in the stomachs of laboratory animals (Fox J. G., Lee A., Gastric Campylobacter-like organisms: their role in gastric disease in laboratory animals. Lab Animal Sci. 1989; 39: 543–553). While *H. pylori* infection is extremely common in both children and adults in many countries throughout the world, many individuals remain infected for years without developing symptoms of gastritis or ulcer disease. Reports have also appeared regarding a possible association between *H. pylori* infection and the development of gastric carcinoma (Parsonnett J., Friedman G. D., Vandersteen M. A., Chang Y., Vogelman J. H., Orentreich N., Sibley R. K., *Helicobacter pylori* infection and the dsk of gastric carcinoma, N. Engl. J. Med. 1991; 325: 1127–1131 and Nomura A., Stemmermann G. N., Chyou P. H., Kato I., Perez-Perez G., Blaser M. J., *Helicobacter pylori* infection and gastric carcinoma among Japanese Americans in Hawaii. N. Engl. J. Med. 1991; 325: 1132–1136).

Histological studies have determined that *H. pylori* colonizes the mucus layer overlying the epithelial cells in the antral region of the stomach and does not appear to invade gastric tissue. While many antimicrobial agents exist with good activity against *H. pylori* in vitro, evaluation of single agents in clinical trials have not resulted in consistent long-term eradication of the organism from the upper gastrointestinal tract. Results from trials with two or more antibiotics, however, indicate that eradication of *H. pylori* is associated with both the resolution of gastritis and significant decreases in relapse rate of duodenal ulcers compared to treatment with H2 antagonists alone. The most effective treatment regimen currently available involves a 2-week course of triple therapy consisting of a bismuth compound together with metronidazole and either tetracycline or amoxycillin. However, there are problems associated with the triple therapy approach to eradicating *H. pylori*, such as non-compliance due to the taste and number of tablets and capsules needed, the onset of side effects such as nausea, diarrhea and dizziness, and the ineffectiveness against antibiotic-resistant strains of *H. pylori*. Other approaches include the use of sulfated glyceroglucolipids (U.S. Pat. No. 5,116,821). Collectively, these studies indicate that better ways of achieving consistent long-term eradication of *H. pylori* are needed.

The unsaturated fatty acids arachidonic acid and ω-3 linolenic acid have been reported to have an inhibitory effect on *H. pylori* (Hazell S. L., Graham D. Y., Unsaturated Fatty Acids and Viability of *Helicobacter* (Campylobacter) *pylori J. Clin. Microbial.* 1990; 1060–61; Thompson L., Cockayne A., Spiller R. C. Inhibitory Effect of W-3 linolenic Acid on the Growth of *Helicobacter pylori*, Abstract PL4 V Workshop on Gastroduodenal Pathology and *Helicopter pylori*, Jul. 5–7, 1992, In Irish Journal of Medical Science). Heretofore, the use of monoglycerides of $C_4$–$C_{17}$ fatty acids to inhibit *Helicobacter pylori* has been unknown.

SUMMARY OF THE INVENTION

I have surprisingly discovered that monoglycerides containing $C_8$–$C_{16}$ fatty acids are effective in inhibiting the gram-negative bacterial pathogen Helicobacter. All Helicobacter species capable of causing gastric problems such as dyspepsia, ulcers or carcinoma are contemplated. At the present time *H. pylori* is most commonly associated with such gastric problems. By the term "inhibiting" or various modifications thereof is meant suppression, control, kill, stasis or any interference with the growth of Helicobacter. Thus, the present invention is directed to a method for inhibiting Helicobacter in a subject in need of treatment comprising administering to said subject an effective amount of at least one monoglyceride containing a $C_8$–$C_{16}$ saturated or unsaturated fatty acid.

In addition, the present invention is directed to a nutritional composition comprising at least one monoglyceride $C_8$–$C_{16}$ saturated or unsaturated fatty acid in an amount effective to inhibit Helicobacter.

We have also discovered that administration of a $C_{12}$ free fatty acid is also effective in inhibiting Helicobacter. Therefore, the present invention is also directed to a method for inhibiting Helicobacter in a subject in need of treatment comprising administering to said subject an effective amount of a $C_{12}$ fatty acid. Also, the present invention is directed to a nutritional composition comprising a $C_{12}$ fatty acid in an amount effective to inhibiting Helicobacter.

DETAILED DESCRIPTION OF THE INVENTION

Figure 1:
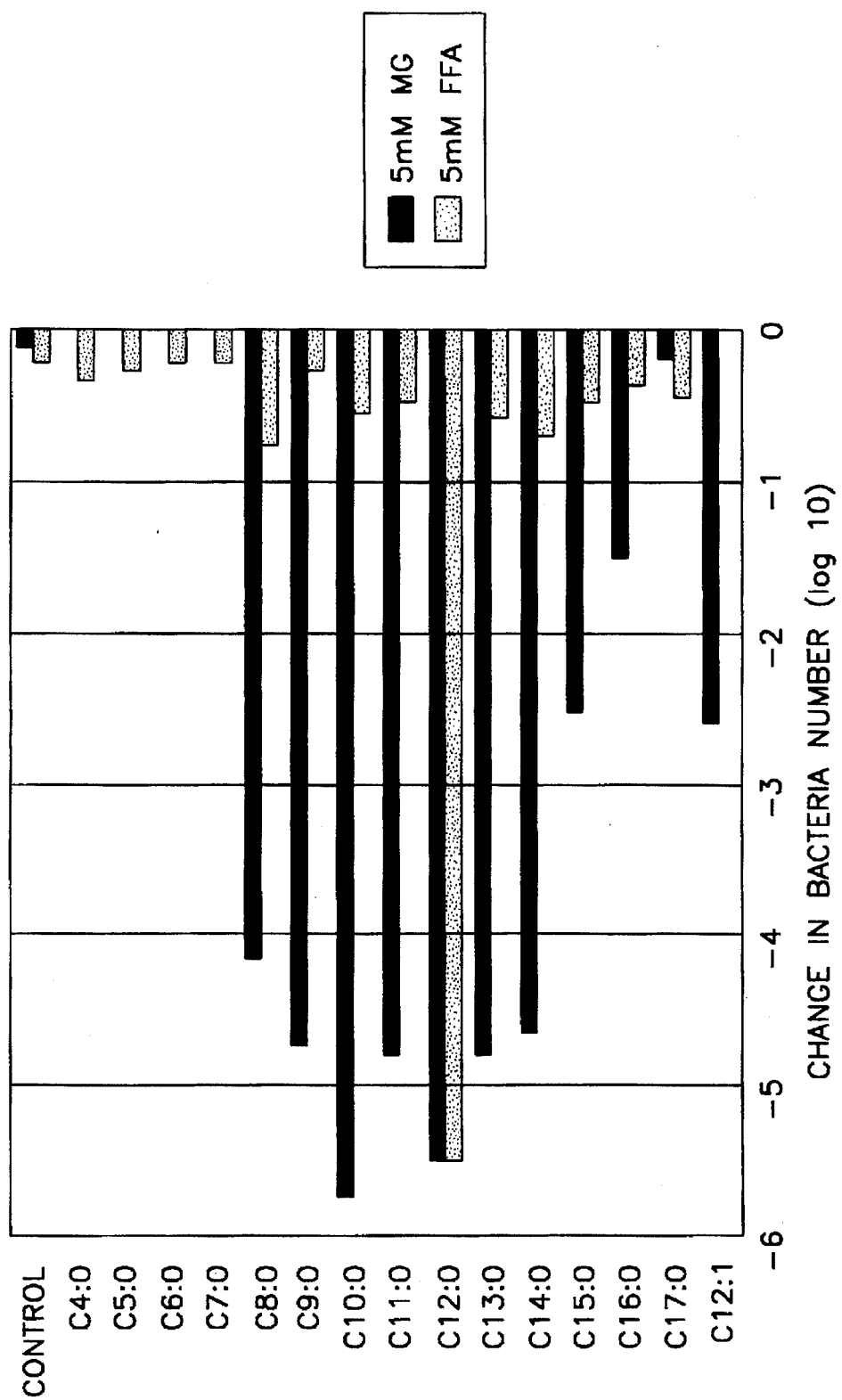
FIG. 1. Effect of monoglyceride and fatty acid chain size on killing activity for *Helicobacter pylori*.

The monoglycerides useful in the present invention are glycerol moieties attached by ester or ether linkage to either saturated or unsaturated fatty acids having from 8 to 16 carbon atoms ($C_8$–$C_{16}$) or to either saturated or unsaturated fatty alcohols having from 8 to 16 carbon atoms ($C_8$–$C_{16}$). Preferred monoglycerides of the invention are saturated. More preferred compounds include $C_8$–$C_{15}$ saturated fatty acids, and most preferably from $C_8$–$C_{14}$ saturated fatty acids. Such monoglycerides include monocaprylin, monopelargonin, monocaprin, monoundecanoin, monolaurin, monotridecanoin, monomyristin, monopentadecanoin and monopalmitin. Preferred monoglycerides are monocaprin, monocaprylin, monopelargonin, monoundecanoin, monotridecanoin, monomyristin, and monolaurin. Also useful according to the invention is the use of the saturated, free $C_{12}$ fatty acid, lauric acid.

The fatty acids and monoglycerides of the composition of the invention can be obtained from a group of readily available animal and plant lipid sources. Desirable monoglycerides that are not commercially available can be prepared by esterification of free fatty acids or derivatives thereof with glycerol according to known procedures. Suitable derivatives of fatty acids include pharmacologically acceptable salts of alkali metals. Examples of such salt forms that would be useful according to the invention include the lithium and sodium salts of the fatty acids. Other fatty acid derivatives useful herein include ester derivatives of fatty acids that are well known to those skilled in the art. Useful examples of such derivatives include butyl-, ethyl-, and methyl-esters of a desirable fatty acid.

The subjects are preferably humans having gastric infections or are at risk for developing gastric infection with *Helicobacter pylori* or other Helicobacter species. Typical effective amounts of one or more monoglyceride is about 0.001 g to about 4.30 g, preferably about 0.002 g to about 3.40 g, and more preferably about 0.003 g to about 2.50 g per kilogram (kg) of body weight per day.

The monoglycerides and/or lauric acid of the invention are administered in such a manner to allow exposure to the gastric mucosa. Therefore, oral administration or tube feeding are convenient forms of administration.

The monoglycerides and lauric add of the invention can be conveniently administered in a nutritional composition. Nutritional compositions of the invention are preferably nutritionally complete.

The compositions of the invention can include infant formulas or enteral nutritional formulas for adults and children. Examples of commercially available nutritional products into which the lauric acid or the monoglycerides of the invention can be conveniently incorporated are described below. Examples of infant formulas include: Enfamil®, milk based formula; Gerber®Baby Formula, milk based formula; Enfapro®, milk based formula; Prosobee®, soy based formula; Gerber® Soy Baby Formula, soy based formula; Nutramigen®, hypoallergenic protein hydrolysate formula; Pregestimil®, hypoallergenic protein hydroysate formula. Examples of enteral nutritional formulas include: Sustacal®, nutritionally complete oral supplement; Sustacal Plus® high calorie, nutritionally complete food oral supplement; Boost®, nutritionally complete oral supplement; Nutrament®, nutritionally complete oral supplement; Isocal®, nutritionally complete, isotonic oral or tube feeding formula; Isocal HN®, nutritionally complete, isotonic, high nitrogen tube feeding formula; Kindercal™, nutritionally complete oral or tube feeding formula designed for children; Ultracal®, nutritionally complete, high nitrogen tube feeding formula with fiber; TraumaCal®, nutritionally complete, high nitrogen, reduced carbohydrate oral or tube feeding formula; Respalor™, nutritionally complete, high calorie oral or tube feeding formula designed for pulmonary patients; Lipisorb®, nutritionally complete oral or tube feeding formula designed for patients with fat malabsorption; and Criticare HN, nutritionally complete, high nitrogen elemental tube feeding formula. These products are available from Mead Johnson & Company, Evansville, Ind., U.S.A. Examples of other commercially available products into which the monoglycerides of the invention may be incorporated are described hereinbelow. From Ross Laboratories, Columbus, Ohio, U.S.A., products include: Similac®, milk based infant formula; Isomil®, soy based infant formula; Ailmenturn®, hypoallergenic, casein hydrolysate formula; Ensure®, nutritionally complete oral supplement; Advera®, nutritionally complete oral and tube feeding formula; and Pediasure®, nutritionally complete oral or tube feeding formula designed for children. From Carnation, products include Carnation Good Start®, partially hydrolyzed whey infant formula, Carnation Follow-On formula, milk based infant formula and Carnation Nutren®, nutritionally complete oral or tube feeding formulas. Products from Wyeth Laboratories, Philadelphia, Pa., U.S.A. include SMA®, milk based infant formula, and Nursoy®, soy based infant formula. Products available from Sandoz, East Hanover, N.J., U.S.A. include Resource®, nutritionally complete high calorie, oral or tube feeding formula.

The nutritional composition contains an amount of at least one monoglyceride of a $C_8$–$C_{16}$ fatty acid effective to inhibit Helicobacter. A typical amount of monoglyceride in the nutritional composition of the invention is about 0.05 g to about 10.0 g per 100 calories of composition, preferred is about 0.1 g to about 8.0 g per calories of composition, and more preferred is about 0.2 g to about 6.0 g per 100 calories of composition.

The composition of the invention is preferably nutritionally complete; however, nutritional supplements and the like are also contemplated. Such nutritional supplements may be administered in the form of capsules, tablets, pills, syrups, or powdered composition as is well known to those skilled in the art. By the term "nutritionally complete" is meant that the composition contains adequate nutrients to sustain healthy human life for extended periods. The composition can be cow milk-based, soy-based, or based on other nutrients. The caloric density of the nutritionally complete composition of the invention contains from 15 to 60 calories per fluid ounce in a ready-to-feed form. The nutritional composition of the invention can be an infant formula or an adult enteral composition that is intended to come into contact with the gastric contents of the stomach and thus prevent colonization of Helicobacter or inhibit Helicobacter already present. Therefore, the method and composition of the invention utilize either a therapeutically effective amount or a prophylactically effective amount. The composition of the invention can be administered via the normal oral route or via tube feeding.

The composition of the invention contains ingredients which are designed to meet the nutritional needs of mammals, especially humans, such as a protein (amino acid) source, a lipid source, and a carbohydrate source. Typically milk, skim milk, casein, hydrolyzed casein, hydrolyzed whey protein, whey, vegetable protein concentrate (e.g. soy protein isolate), hydrolyzed vegetable protein (e.g. soy), animal fats, vegetable oils, starch, sucrose, fructose, lactose and/or corn syrup solids will be added to the composition to supply part or all of the amino acids and/or protein, lipid, and carbohydrate as well as other nutrients such as vitamins and minerals.

The composition of the invention preferably comprises about 0.5 g to about 10.0 g protein, about 0.1 g to about 9.0 g lipid, and about 6.0 g to about 25.0 g total carbohydrate per 100 calories of composition. More preferably, the composition of the invention comprises about 1.0 g to about 8.0 g protein, about 0.2 g to about 8.0 g lipid, and about 7 g to about 22.9 g carbohydrate per 100 calories of composition. Most preferably, the composition of the invention comprises about 1.8 g to about 6.2 g protein, about 0.4 g to about 7.0 g lipid, and about 8.0 g to about 20.0 g carbohydrate per 100 calories of composition.

The carbohydrate component of the composition of the invention, if present, can be any suitable carbohydrate known in the art to be suitable for use in nutritional compositions. Typical carbohydrates include sucrose, fructose, xylitol, glucose, maltodextrin, lactose, corn syrup, corn syrup solids, rice syrup solids, rice starch, modified corn starch, modified tapioca starch, rice flour, soy flour, and the like. Part of the carbohydrate can be fiber such as soy fiber, pectin, resistant starch, oat fiber, pea fiber, guar gum, gum acacia, modified cellulose, and the like.

If lipid is present it can be any lipid or fat known in the art to be suitable for use in nutritional compositions. Typical lipid sources include milk fat, safflower oil, canola oil, egg yolk lipid, olive oil, cotton seed oil, coconut oil, palm oil, palm kernel oil, soybean oil, sunflower oil, fish oil and fractions of all above oils derived thereof such as palm olein, medium chain triglycerides (MCT), and esters of fatty acids wherein the fatty acids are, for example, arachidonic acid, linoleic acid, palmitic acid, stearic acid, docosahexaeonic acid, eicosapentaenoic acid, linolenic acid, oleic acid, lauric acid, capric acid, caprylic acid, caproic acid, and the like. High oleic forms of various oils are also contemplated to be useful herein such as high oleic sunflower oil and high oleic safflower oil.

If protein is present it can be any protein and/or amino acid mixture known in the art to be suitable for use in nutritionally complete compositions. Typical protein sources are animal protein, vegetable protein such as soy protein, milk protein such as skim milk protein, whey protein and casein, and amino acids (or salts thereof) such as isoleucine, phenylalanine, leucine, lysine, methionine, threonine, tryptophan, arginine, glutamine, taurine, valine, and the like. Preferred protein sources are whey protein, sodium caseinate or calcium caseinate optionally supplemented with amino acids. For some applications a preferred protein source is hydrolyzed protein (protein hydrolysate) optionally supplemented with amino acids.

The protein hydrolysate useful in the invention may be any suitable protein hydrolysate utilized in a nutritional formula such as soy protein hydrolysate, casein hydrolysate, whey protein hydrolysate, other animal and vegetable protein hydrolysates, and mixtures thereof. The protein hydrolysate of the composition of the invention is preferably a soy protein, whey protein, or a casein protein hydrolysate comprising short peptides and amino acids, optionally supplemented with additional amino acids. In a preferred embodiment, the protein hydrolysate useful in the invention contains a high percentage of free amino acids (e.g. greater than 40%) and low molecular weight peptide fragments.

The hydrolyzed protein of the composition of the invention is also preferably supplemented with various free amino acids to provide a nutritionally balanced amino content. Examples of such free amino acids include L-tryptophan, L-methionine, L-cystine, L-tyrosine, and L-arginine.

Nutritionally complete compositions contain all vitamins and minerals understood to be essential in the daily diet and these should be present in nutritionally significant amounts. Those skilled in the art appreciate that minimum requirements have been established for certain vitamins and minerals that are known to be necessary for normal physiological function. Practitioners also understand that appropriate additional amounts (overages) of vitamin and mineral ingredients need to be provided to compensate for some loss during processing and storage of such compositions. The composition of the invention preferably contains at least 100% of the U.S. Recommended Daily Allowance (RDA) in 500 to 4000 cal of composition, preferably to 600 to 3000 cal of composition.

To select a specific vitamin or mineral compound to be used in the composition requires consideration of that compound's chemical nature regarding compatibility with the processing and shelf storage.

Examples of minerals, vitamins and other nutrients optionally present in the infant formula of the invention include vitamin A, vitamin $B_6$, vitamin $B_{12}$, vitamin E, vitamin K, vitamin C, vitamin D, inositol, taurine, folic acid, thiamine, riboflavin, niacin, biotin, pantothenic acid, choline, calcium, phosphorous, iodine, iron, magnesium, copper, zinc, manganese, chloride, potassium, sodium, beta-carotene, nucleotides, selenium, chromium, molybdenum, and L-carnitine. Minerals are usually added in salt form. In addition to compatibility and stability considerations, the presence and amounts of specific minerals and other vitamins will vary somewhat depending on the intended consumer population.

The composition of the invention also typically contains emulsifiers and/or stabilizers such as lecithin (e.g., egg or soy), modified lecithin (e.g., enzyme or acetylated), carrageenan, xanthan gum, mono- and diglycerides, guar gum, carboxymethyl cellulose, stearoyl lactylates, succinylated monoglycerides, sucrose esters of fatty acids, diacetyl tartaric acid esters of monoglycerides, polyglycerol esters of fatty acids, or any mixture thereof.

The composition of the invention can be prepared by use of standard techniques known in the nutritional art, for example by techniques analogous to those disclosed in U.S. Pat. Nos. 4,670,268; 4,497,800; 5,104,677; 5,223,285, the disclosures of which are incorporated herein by reference in their entirety. Useful monoglycerides or fatty acids can be incorporated into the composition of the invention by standard techniques known in the nutritional art. Examples of such techniques include dry blending into powder premixes, addition in the form of liquid product emulsifiers, addition with alternative oils and lipid mixtures, or direct addition to liquid product during routine manufacturing processes.

The composition of the invention can be sterilized, if desired, by techniques known in the art, for example, heat treatment such as autoclaving or retorting, irradiation, and the like, or processed and packaged by aseptic technology.

The composition of the invention can be packaged in any type of container known in the art to be useful for storing nutritional products such as glass, lined paperboard, plastic, coated metal cans and the like.

In the method of the invention for inhibiting Helicobacter, or the composition of the invention may consist of one or more monoglycerides or lauric acid in free form or as part of a diglyceride or triglycedde that may be modified during digestion by salivary and gastric secretions to liberate or generate the free and active form of the monoglyceride or lauric acid.

In the method of the invention it is contemplated that effective antibiotics and other substances, such as bismuth, metronidazole, tetracycline, ampicillin, or benzimidazole proton pump inhibitors such as omeprazole, that are known to be effective against Helicobacter may be used in conjunction with the monoglycerides of the invention.

The frequency of development of resistance to the MG and FFA useful in the present invention by *H. pylori* is preferably less than with other commonly used antimicrobial agents, for example, tetracycline and metronidazole.

The following examples are to illustrate the invention but should not be interpreted as a limitation thereon.

EXAMPLE 1

Inhibition of *Helicobacter pylori* by Monoglycerides

Stock cultures of *H. pylori* were maintained on horse blood agar at 3–5 day intervals in GasPak jars. Test strains of *H. pylori* were grown in 10 ml of Brucella broth containing 10% fetal bovine serum at 37° C. under microaerophilic conditions on a gyratory platform shaker. Following incubation until appropriate growth was apparent, bacterial cells were washed in 2.8% (w/v) Brucella broth and adjusted to a desired concentration by routine turbidimetric methods. Washed bacterial cells were then suspended at $5-10 \times 10^5$ CFU/ml in 2% (w/v) Brucella broth (pH 7.2) with various concentrations of FFA or MG and incubated at 37° C. for 1 hour. Control samples consisted of test bacteria incubated under similar conditions in Brucella broth without FFA or MG. The number of viable bacteria remaining in test mixtures was determined by standard plate counting procedures on chocolate agar.

The effect of medium chain ($C_8-C_{12}$) FFA and MG on viability of *H. pylori* is shown in Table 1. Test strains of *H. pylori* were originally obtained from human subjects and were designated HP-2 (ATCC 43579), HP-4 (ATCC 43629), and HP-5 (ATCC 49503). No change in viable cell numbers was observed in control samples following the 1 hour incubation. Test strains of *H. pylori* were the most sensitive to $C_{10}$ MG (monocaprin), $C_{12}$ MG (monolaurin), and $C_{12}$ FFA (lauric acid), showing 10,000-fold or greater reductions in cell numbers after a 1 hour incubation. All 3 test strains were slightly less sensitive to $C_8$ MG (monocaprylin), showing 1000-fold or greater reductions in cell numbers. None of the test strains of *H. pylori* were affected by up to 5 mM $C_8$ FFA or $C_{10}$ FFA.

EXAMPLE 2

Monoglycerides in Nutritional Compositions

MG's have been used in the food industry since the 1930's for their emulsification and antifoaming properties. In addition, MG are added to pediatric and adult nutritional products for emulsification purposes. Other potential sources of MG in these products include lecithin and the lipid or fat blends used in formulating these products. The MG content of representative pediatric and adult nutritional products was evaluated using standard thin layer separation and gas chromatographic methods. Results indicate that the total MG content typically ranges from 10.4–921.2 mg per liter of nutritional composition (Table 2). The MG content of powder products is typically lower than that of liquid nutritional products; range in powder products, 10.4–20.2; range in liquid products, 22.3–921.2. The fatty acid composition of the MG found in pediatric and adult nutritional products is shown in Tables 3 and 4. Fatty acids found in the highest concentrations in MG in nutritional products include $C_{18:0}$ (stearic), $C_{16:0}$ (palmitic), and $C_{14:0}$ (myristic). The highest levels of medium chain fatty acids in MG of pediatric nutritional products were as follows: $C_{8:0}$ (caprylic), 1.8 mg/L; $C_{10:0}$ (capric), 1.0 mg/L; $C_{12:0}$ (lauric), 5.7 mg/L. The highest levels of medium chain fatty acids in MG in adult nutritional products were as follows: $C_{8:0}$ (caprylic), 4.4 mg/L; $C_{10:0}$ (capric), 2.1 mg/L; $C_{12:0}$ (lauric), 1.2 mg/L. Collectively, these data indicate that pediatric and adult nutritional products typically contain $C_{8:0}$, $C_{10:0}$, and $C_{12:0}$ MG at less than 10 mg/L (approximately 0.05 mM).

EXAMPLE 3

Inhibitory Activity of Monoglycerides in Nutritional Compositions

In order to evaluate the anti-infective potential of MG in nutritional compositions, several experimental products were prepared with varying levels of MG for evaluation of antimicrobial properties. Nutritional compositions can be formulated with different fat and protein sources. In Table 5, three examples of MG supplemented nutritional compositions are presented. Formulation I (Sustacal) is made with soy oil and casein and soy protein at about 75:25 ratio. Formulation II (Nutrament) is prepared with soy oil and milk proteins containing casein and whey proteins at about 90:10 ratio. Formulation III (Ultracal) is prepared with soy oil and MCT oil and casein as the sole source of protein.

An in vitro assay was used to evaluate the inhibitory properties of nutritional compositions containing medium chain (C8–C12) FFA and MG for *Helicobacter pylori*. Stock cultures of *H. pylori* (ATCC 43629) were grown in 10 ml of Brucella broth containing 10% fetal bovine serum at 37° C. under microaerophilic conditions on a gyratory platform shaker. Following incubation until appropriate growth was apparent, bacterial cells were washed in 2.8% (w/v) Brucella broth and adjusted to a desired concentration by routine turbidimetric methods. Wash bacterial cells were suspended at approximately $5 \times 10^5$ CFU/mL in prototype nutritional products containing MG or FFA and incubated at 37° C. for 1 hour. Control samples consisted of test bacteria incubated under similar conditions in nutritional products without FFA or MG. The number of viable bacteria remaining in test mixtures after 1 hour was determined by standard plate counting procedures on either chocolate agar or horse blood agar plates.

The effect of medium chain ($C_8$–$C_{12}$) FFA and MG in prototype nutritional compositions on the viability of *H. pylori* is shown in Table 6. Nutritional compositions that were tested consisted of Formulations I, II and III (Table 5) containing medium-chain FFA or MG at levels ranging from 5–20 mM. The results are in Table 6. Both $C_8$ and $C_{10}$ FFA (caprylic acid, capric acid) were not inhibitory at levels as high as 20 mM. Lauric acid ($C_{12}$ FFA) caused 1000-fold or greater reductions in cell viability at 20 mM levels in 2 of 3 example formulations. Lower levels of $C_{12}$ FFA were not inhibitory. All three MG tested ($C_8$, $C_{10}$, $C_{12}$) caused 1000-fold or greater reductions in viability of *H. pylori* when tested at 10 mM for 1 hour. $C_{10}$ and $C_{12}$ MG (monocaprin, monolaurin) caused similar changes when tested at 5 mM.

EXAMPLE 4

Bacterial Activity of MG and FFA of Varying Chain Length

To define the relationship between carbon chain length and potential anti-infective activity of MG and FFA for *H. pylori*, odd- and even-chain MG and FFA having carbon chain lengths ranging from $C_{4:0}$ to $C_{17:0}$ were compared for bactericidal activity against *H. pylori*. The inhibitory activity of MG and FFA were evaluated against *H. pylori* laboratory strain HP-4 (ATCC 43629) by the methods described in Example 1. Washed bacterial cells were suspended in Brucella broth ($\sim 5 \times 10^5$ CFU/mL) containing test MG or FFA and incubated at 37° C. for 1 hour. Serial dilutions of bacterial suspensions were prepared and plated on horse blood agar plates to determine the number of viable cells that survived treatment.

The effect of odd-and even-chain MG and FFA on viability of *H. pylori* ranging from 10-fold (1 log unit) to greater than 10,000-fold (4 log unit) were observed for MG with chain lengths ranging from $C_8$ to $C_{16}$ ($C_{8:0}$, $C_{9:0}$, $C_{10:0}$, $C_{11:0}$, $C_{12:0}$, $C_{13:0}$, $C_{14:0}$, $C_{15:0}$, $C_{16:0}$). Shorter chain MGs ($C_{4:0}$ to $C_{7:0}$) were not tested due to lack of availability. The bactericidal activity of a $C_{12:1}$ MG containing a single double bond in the 1 position was less active than the unsaturated form ($C_{12:0}$), suggesting that saturated forms are more bactericidal than unsaturated MGs. In contrast to the bactericidal activity of MG, lauric acid ($C_{12:0}$ FAA) was the only FFA among those tested ($C_{4:0}$ to $C_{17:0}$) that showed bactericidal activity for *H. pylori*.

EXAMPLE 5

Generation of Resistance to MG or FFA by *H. pylori*

The ability of *H. pylori* to develop resistance to the bactericidal activity of MG and FFA was evaluated because of reports indicating that emergence of resistance to metronidazole and other antimicrobial agents is a problem in treatment of *H. pylori* infections (Glupczynski, Y., A. Burette, E. de Koster, et al., Metronidazole resistance in *Helicobacter pylori* (letter), Lancet 1990; 335:976–977; Marshall, B. J. Treatment strategies for *Helicobacter pylori* infection, Gastroenterol, Clinics North Amer. 1993; 22:183–198). The frequency of innate resistance to $C_{10:0}$ MG, $C_{12:0}$ MG, and $C_{12:0}$ FFA among three strains of *H. pylori* (HP-2, HP-4, HP-5) was evaluated at multiples of the minimal inhibitory concentration (MIC) of test agents and compared to the innate resistance of test strains to tetracycline and metronidazole. The frequency of in vitro resistance development was determined by the method of Fernandes, et al. (Fernandes, P. B., C. W. Hanson, J. M. Stamm, C. Vojtko, N. L. Shipkowitz, and E. St. Martin. The frequency of in vitro resistance development to fluoroquinolones and the use of murine pyelonephritis model to demonstrate selection of resistance in vivo. J. Antimicrob. Chemother. 1987; 19:449–465). An overnight culture of *H. pylori* was washed and plated on horse blood agar plates ($\sim 10^7$ to $10^8$ CFU/plate) containing from two to ten times the estimated MIC of test MG, FFA, or antibiotics. Plates were incubated for five days at 37° C. under microaerophilic conditions. The number of resistant colonies were quantitated and compared to the number of viable cells in the initial inoculum as determined by standard dilution plate counting on horse blood agar plates without antimicrobial agents.

Preliminary studies determined that the MIC of $C_{10:0}$ MG, $C_{12:0}$ MG, and $C_{12:0}$ FFA for *H. pylori* was approximately 60, 15, and 50 mg/L, respectively. In general, the frequency of innate resistance among *H. pylori* strains was consistently higher for metronidazole and tetracycline than for MG and FFA (Table 7). While the pattern of sensitivity to metronidazole and tetracycline varied among the three test strains of H. pylori, the number of variants resistant to metronidazole or tetracycline when tested at 5 times the MIC ranged from about 50 to greater than 1000 per $10^8$ cells for each strain of H. pylori (frequency of resistance, $10^{-5}$ to 10-7). As expected, frequencies of innate resistance decreased with increasing concentration of test antibiotics. In contrast, no resistant variants of H. pylori were found when 108 cells were plated on media containing $C_{10:0}$ MG, $C_{12:0}$ MG or $C_{12:0}$ FFA at concentrations as low as two times the MIC (frequency of resistance, $<1 \times 10^{-8}$).

The restricted host range of Helicobacter pylori has hampered the development of a widely accepted animal model of H. pylori infection. Although H. pylori has been shown to infect germ-free piglets and nonhuman primates, such models are not only expensive and inconvenient, but differences have been reported for the histopathological changes that occur compared to human disease. Other animal models of Helicobacter infection have been described based on bacteria similar to H. pylori that have been found in the gastric mucosa of various animals such as the ferret, cat, and monkey. One such model involves the inoculation of adult mice with Heicobacter felis (Fox, J. G., J. C. Murphy, N. S. Taylor, A. Lee, Z. Kabob, and L. Pappo., Local and systemic immune responses in murine Helicobacter felis active chronic gastritis., Infect. Immun. 1993; 61:2309–2315; Dick-Hegedus, E., and A. Lee. Use of a mouse model to examine anti-Helicobacter pylori agents., Scand. J. Gastroenterol. 1991;26:909–915).

Preliminary studies were conducted to evaluate the antiinfective activity of MG and FFA against Helicobacter infection in vivo using the H. felis infected mouse model. Adult mice were challenged with ~1×10$^7$ CFU of H. felis and maintained on a nutritionally complete liquid diet. Two weeks later mice were randomized into treatment groups and maintained on liquid diet alone or the same diet supplemented with $C_{10:0}$ MG or $C_{12:0}$ MG at a level of 1,5, or 10 mM. Gastric colonization with H. felis in mice was determined 1 and 3 weeks later by evaluation of urease activity (Hazell, S. L., T. J. Barody, A. Gal, and A. Lee., Campylobacter pyloridis gastritis I: Detection of urease as a marker of bacterial colonization and gastritis. Am. J. Gastroenterol. 1987; 82: 292–296) and histopathological assessment of bacterial infection in gastric tissues.

Approximately 90% of control mice fed liquid diet alone showed evidence of H. felis infection (i.e. urease positive, histology positive) following 1 week of treatment. Groups of mice fed diet containing $C_{10:0}$ MG showed dose-related reductions in the number of urease and histology positive mice, suggesting a reduction in H. felis infection by treatment of infected mice with $C_{10:0}$ MG. Lower levels of infection were also observed among those mice that were urease positive and given $C_{10:0}$ MG compared to control mice (histology score). By three weeks after initiation of treatment, numbers of urease positive and histology positive mice were comparable to the number observed in the infected control group (~80–100%) while the histology score remained lower in mice that received 10 mM $C_{10:0}$ MG Results from a second study showed no significant reduction in H. felis infection in adult mice after daily treatment by intragastric gavage for 1 or 3 weeks with $C_{10:0}$ MG (1.4 or 2.8 mg/day).

Several reasons exist to explain why oral administration of MG was not completely successful in eradicating H. felis infection in mice in these preliminary studies. First, the total amount of MG administered to mice may not have been sufficient to completely clear infection; additional studies would be needed to determine the effect of higher levels of MG. Secondly, lipase activity and absorptive mechanisms in the stomachs of test mice may have decreased the amounts of MG available to exert an inhibitory effect on H. felis. Finally, H. felis has a propensity to colonize deep within the gastric pit region of the mouse stomach which might limit exposure to MG present in the lumen of the stomach during feeding. In contrast, it has been reported that H. pylori colonizes most frequently in the mucus layer or in close proximity to the surface of gastric epithelial cells (Neri, M., D. Susi, I. Bovani, F. Laterza, A. Mezzetti, and F. Cuccurullo., Bacterial mucosal infiltration in Helicobacter pylori-associated gastritis: histological and clinical consequences. Am. J. Gastroenterol. 1994; 89:1801–1805) which might allow for greater exposure to luminal MG.

TABLE 1

INHIBITORY ACTIVITY OF MEDIUM-CHAIN MONOGLYCERIDES AND FATTY ACIDS FOR *HELICOBACTER PYLORI*

| MONOGLYCERIDE OR FATTY ACID | FATTY ACID CHAIN LENGTH | REDUCTION IN NUMBER OF VIABLE *H. PYLORI* CELLS (CFU/mL) | | |
|---|---|---|---|---|
| | | ATCC #43579 | ATCC #43629 | ATCC #49503 |
| Caprylic Acid 1 mM | C8 | None | None | None |
| Caprylic Acid 5 mM | | None | None | None |
| Capric Acid 1 mM | C10 | None | None | None |
| Capric Acid 5 mM | | None | None | None |
| Lauric Acid 1 mM | C12 | >100,000-fold | >50,000-fold | >10,000-fold |
| Lauric Acid 5 mM | | NT | NT | NT |
| Monocaprylin 1 mM | C8 | None | None | None |
| Monocaprylin 5 mM | | >4,000-fold | >3,000-fold | >40,000-fold |
| Monocaprin 1 mM | C10 | >100,000-fold | >60,000-fold | >30,000-fold |
| Monocaprin 5 mM | | NT | NT | NT |
| Monolaurin 1 mM | C12 | >100,000-fold | >50,000-fold | >30,000-fold |
| Monolaurin 5 mM | | NT | NT | NT |

NT = Not Tested.
NOTE: No change in number of viable *H. pylori* defined as less than 5-fold reduction in CFU/mL.

TABLE 2

TOTAL FAT AND MONOGLYCERIDE CONTENT OF PEDIATRIC AND ADULT NUTRITIONAL PRODUCTS

| PRODUCT | FORM | TOTAL FAT (% W/V) | TOTAL MG (mg/L) |
|---|---|---|---|
| Enfamil | Powder | 4.11 | 18.54 |
| ProSobee | Liquid | 3.66 | 237.90 |
| Enfapro | Powder | 2.94 | 20.23 |
| Carnation Follow-on | Liquid | 6.01 | 31.70 |
| Nutramigen | Powder | 3.04 | 10.40 |
| Pregestimil | Powder | 4.24 | 15.70 |
| Pediasure | Liquid | 5.13 | 372.63 |
| Kindercal | Liquid | 4.30 | 588.99 |
| Sustagen Mighty Drink | Powder | 1.07 | 14.56 |
| Sustacal | Liquid | 2.40 | 37.40 |
| Sustacal Plus | Liquid | 5.40 | 37.43 |
| Ultracal With Fiber | Liquid | 3.73 | 356.48 |
| Isocal HN | Liquid | 5.06 | 244.26 |
| Lipisorb | Powder | 5.12 | 19.42 |
| Lipisorb | Liquid | 4.89 | 921.23 |
| Boost | Liquid | 2.91 | 22.30 |
| Nutrament | Liquid | 2.81 | 24.75 |
| Traumacal | Liquid | 5.98 | 24.70 |
| Respalor | Liquid | 6.61 | 30.30 |
| Advera | Liquid | 2.72 | 176.88 |

NOTE: Measurements at normal use dilution.

TABLE 3

FATTY ACID CONTENT OF MONOGLYCERIDES IN PEDIATRIC NUTRITIONAL PRODUCTS

| PRODUCT | FATTY ACID CONTENT (mg/L) | | | | | | | |
|---|---|---|---|---|---|---|---|---|
| | C8:0 | C10:0 | C12:0 | C14:0 | C16:0 | C18:0 | C18:1 | C18:2N6 |
| Enfamil | 0.14 | 0.14 | 1.41 | 1.19 | 4.48 | 0.71 | 3.5 | 5.9 |
| ProSobee | 0.02 | 0.33 | 5.66 | 5.00 | 125.14 | 83.5 | 7.0 | 8.6 |
| Enfapro | 0.07 | 0.25 | 0.48 | 0.8 | 7.6 | 0.7 | 5.5 | 4.7 |
| Carnation Follow-on | 0.0 | 0.5 | 0.8 | 1.0 | 11.3 | 1.8 | 9.5 | 5.6 |
| Nutramigen | 0.05 | 0.2 | 0.1 | 0.04 | 2.3 | 0.0 | 2.4 | 5.3 |
| Pregestimil | 1.8 | 1.0 | 0.1 | 0.02 | 3.4 | 0.0 | 3.6 | 5.7 |
| Pediasure | 0.15 | 0.6 | 0.2 | 1.1 | 41.2 | 319.8 | 4.3 | 3.4 |
| Kindercal | 0.6 | 0.3 | 2.1 | 7.0 | 254.4 | 314.9 | 3.4 | 3.6 |
| Sustagen Mighty Drink | 0.44 | 0.6 | 0.6 | 2.6 | 6.7 | 0.8 | 1.7 | 0.5 |

NOTE: Negligible amounts found for C15:0, C16:1, C18:3N6, C18:3N3, C18:4N3, C20:0, C20:1, C22, C23, C24.

TABLE 4

FATTY ACID CONTENT OF MONOGLYCERIDES IN ADULT NUTRITIONAL PRODUCTS

| PRODUCT | FATTY ACID CONTENT (mg/L) | | | | | | | |
|---|---|---|---|---|---|---|---|---|
| | C8:0 | C10:0 | C12:0 | C14:0 | C16:0 | C18:1 | C18:1 | C18:2N6 |
| Sustacal (RTU) | 0.1 | 0.1 | 0.3 | 0.1 | 7.3 | 3.1 | 8.4 | 16.3 |
| Sustacal Plus | 0.1 | 0.1 | 0.5 | 1.1 | 10.3 | 2.2 | 5.2 | 14.4 |
| Ultracal With Fiber | 4.4 | 1.1 | 0.5 | 2.8 | 109.8 | 144.4 | 1.7 | 4.5 |
| Isocal HN | 1.7 | 0.8 | 0.2 | 1.6 | 72.0 | 74.6 | 2.4 | 4.9 |
| Lipisorb (Powder) | 3.2 | 2.0 | 0.5 | 0.6 | 4.0 | 0.3 | 2.9 | 5.5 |
| Lipisorb (Liquid) | 2.7 | 2.1 | 1.2 | 7.4 | 297.4 | 255.8 | 0.5 | 2.5 |
| Boost | 0.1 | 0.3 | 0.9 | 1.7 | 5.6 | 1.4 | 6.9 | 4.0 |
| Nutrament | 0.1 | 0.3 | 0.4 | 0.9 | 7.5 | 3.0 | 4.1 | 4.7 |
| Traumacal | 0.6 | 0.6 | 0.8 | 1.3 | 7.0 | 4.9 | 3.1 | 5.2 |

TABLE 4-continued

FATTY ACID CONTENT OF MONOGLYCERIDES IN ADULT NUTRITIONAL PRODUCTS

| PRODUCT | FATTY ACID CONTENT (mg/L) | | | | | | | |
|---|---|---|---|---|---|---|---|---|
| | C8: 0 | C10: 0 | C12: 0 | C14: 0 | C16: 0 | C18: 1 | C18: 1 | C18: 2N6 |
| Respalor | 0.6 | 0.2 | 0.7 | 1.1 | 6.8 | 0.3 | 11.2 | 6.6 |
| Advera | 0.2 | 0.0 | 0.2 | 0.4 | 15.0 | 156.1 | 2.5 | 1.1 |

NOTE: Negligible amounts found for C15: 0, C16: 1, C18: 3N6, C18: 3N3, C18: 4N3, C20, C22, C23, C24.

TABLE 5

NUTRITIONAL COMPOSITION WITH MONOGLYCERIDES FORMULATION EXAMPLES

| INGREDIENT | Kg/1000 L |
|---|---|
| FORMULATION I | |
| Casein | 38.04 |
| Corn Syrup Solids | 131.23 |
| Say Protein Isolate | 5.04 |
| Sucrose | 46.49 |
| Soy Oil | 34.24 |
| Lecithin | 2.14 |
| Carrageenan | 0.43 |
| Choline Chloride | 0.63 |
| Ferric Pyrophosphate | 0.04 |
| Calcium Phosphate, Tribasic | 1.24 |
| Potassium Chloride | 1.30 |
| Magnesium Chloride | 1.75 |
| Potassium Citrate | 2.58 |
| Sodium Citrate | 1.58 |
| Ferrous Sulfate, Heptahydrate | 0.01 |
| Dry Vitamin Premix | 0.50 |
| Trace Mineral Premix | 0.07 |
| Vitamin ADEK Premix | 0.08 |
| FORMULATION II | |
| Sucrose | 80.91 |
| Corn Syrup Liquid | 25.80 |
| Soy Protein Isolate | 5.64 |
| Nonfat Milk Solids | 84.10 |
| Soy Oil | 27.74 |
| Caseinate Solids | 9.32 |
| Lecithin | 0.28 |
| Gelcarin MMR | 0.32 |
| Vitamin ADE Premix | 0.11 |
| Magnesium Chloride | 1.02 |
| Magnesium Phosphate, Dibasic | 1.02 |
| Dry Vitamin Premix | 0.26 |
| Trace Mineral Premix | 0.11 |
| FORMULATION III | |
| Caseinate Solids | 48.17 |
| Malto-Dextrin | 124.31 |
| Canola Oil | 26.63 |
| MCT Oil | 18.17 |
| Mono- Diglycerides | 0.66 |
| Lecithin | 0.66 |
| Carrageenan | 0.08 |
| Choline Chloride | 0.66 |
| L-Carnitine | 0.19 |
| Sodium Phosphate, Dibasic | 0.65 |
| Potassium Chloride | 0.71 |
| Magnesium Chloride | 2.48 |
| Calcium Phosphate, Tribasic | 0.96 |
| Sodium Citrate | 0.63 |
| Potassium Citrate | 2.45 |
| Ferrous Sulfate, Heptahydrate | 0.07 |
| Dry Vitamin Premix | 1.40 |
| Trace Mineral Premix | 0.09 |
| Vitamin ADEK Premix | 0.12 |
| Oat Fiber | 4.49 |
| Soy Fiber | 14.77 |

TABLE 6

BACTERIAL ACTIVITY OF MONOGLYCERIDES IN NUTRITIONAL PRODUCTS FOR *HELICOBACTER PYLORI*

| MONOGLYCERIDE OR FATTY ACID | CHANGE IN VIABLE CELL NUMBER (LOG CFU/mL) | | |
|---|---|---|---|
| | SUSTACAL | NUTRAMENT | ULTRACAL |
| Caprylic Acid 5 mM | 0.00 | | 0.06 |
| Caprylic Acid 10 mM | 0.00 | | −0.20 |
| Caprylic Acid 20 mM | 0.02 | −0.21 | −0.81 |
| Capric Acid 5 mM | 0.00 | | 0.03 |
| Capric Acid 10 mM | 0.00 | | −0.03 |
| Capric Acid 20 mM | −0.09 | −0.08 | −0.33 |
| Lauric Acid 5 mM | 0.00 | | 0.33 |
| Lauric Acid 10 mM | 0.05 | | −1.05 |
| Lauric Acid 20 mM | −3.33 | −0.42 | −3.96 |
| Monocaprylin 5 mM | 0.37 | −4.23 | 0.00 |
| Monocaprylin 10 mM | −3.44 | −4.23 | −3.64 |
| Monocaprylin 20 mM | NT | NT | −4.46 |
| Monocaprin 5 mM | −3.78 | −4.00 | −4.40 |
| Monocaprin 10 mM | −3.91 | −4.14 | −4.40 |
| Monocaprin 20 mM | NT | NT | NT |
| Monolaurin 5 mM | −3.41 | −4.23 | −3.04 |
| Monolaurin 10 mM | −3.77 | −3.87 | −4.40 |
| Monolaurin 20 mM | NT | NT | NT |

NT = Not Tested

TABLE 7

Frequency of development of resistance to MG, FFA or antibiotics by *Helicobacter pylori*.

| Test Article | H. pylori Strain | MIC (mg/L) | Frequency of resistant mutants[a] | | |
|---|---|---|---|---|---|
| | | | 2 × MIC | 5 × MIC | 10 × MIC |
| monocaprin (C10:0) | 43579 | 60.0 | <1 | <1 | <1 |
| | 43629 | | <1 | <1 | <1 |
| | 49503 | | <1 | <1 | <1 |
| monolaurin (C12:0) | 43579 | 15.0 | <1 | <1 | <1 |
| | 43629 | | <1 | <1 | <1 |
| | 49503 | | <1 | <1 | <1 |
| lauric acid (C12:0) | 43579 | 50.0 | <1 | <1 | <1 |
| | 43529 | | <1 | <1 | <1 |
| | 49503 | | <1 | <1 | <1 |

TABLE 7-continued

Frequency of development of resistance to MG, FFA or antibiotics by *Helicobacter pylori*.

| Test Article | H. pylori Strain | MIC (mg/L) | Frequency of resistant mutants[a] | | |
|---|---|---|---|---|---|
| | | | 2 × MIC | 5 × MIC | 10 × MIC |
| tetracycline | 43579 | 0.1 | TNTC | TNTC | <1 |
| | 43629 | | >1000 | 242 | <1 |
| | 49503 | | 148 | <1 | <1 |
| metronidazole | 43679 | 2.0 | >1000 | 862 | 518 |
| | 43629 | | 791 | <1 | <1 |
| | 49503 | | >1000 | 48 | <1 |

[a]Number of spontaneous mutants found after incubation of *H. pylori* (~1 × $10^8$ CFU) on horse blood agar containing the indicated concentration of MG, FFA, or antibiotic. Results shown are representative of data obtained from at least 2 individual experiments with each strain of *H. pylori*.

What is claimed is:

1. A method of inhibiting Helicobacter in a subject in need of treatment comprising administering to said subject about 0.001 g to about 4.3 g per kg of body weight per day of at least one monoglyceride of a $C_8$–$C_{16}$ fatty acid.

2. The method of claim 1 wherein said monoglyceride is a monoglyceride of a $C_8$–$C_{15}$ fatty acid.

3. The method of claim 1 wherein said monoglyceride is a monoglyceride of a $C_8$–$C_{14}$ fatty acid.

4. The method of claim 1 wherein the monoglyceride is selected from the group consisting of monocaprylin, monocaprin, monolaurin, monopelargonin, monoundecanoin, monotridecanoin, monomyristin, monopentadecanoin and monopalmitin.

5. The method of claim 1 wherein said monoglyceride is selected from the group consisting of monocaprylin, monocaprin, monopelargonin, monotridecanoin, monoundecanoin, monomyristin, and monolaurin.

6. The method of claim 1 wherein said effective amount is about 0.002 to about 3.4 g per kg of body weight per day.

7. The method of claim 1 wherein said effective amount is about 0.003 g to about 2.5 g per kg. of body weight per day.

8. The method of claim 1 wherein said monoglyceride is orally administered in a nutritional composition.

9. The method of claim 6 wherein said nutritional composition is nutritionally complete.

10. The method of claim 1 wherein said Helicobacter is *H. pylori*.

11. A method for inhibiting Helicobacter in a subject in need of treatment comprising administering to said subject about 0.001 to about 4.3 g per kg of body weight per day of lauric acid.

12. The method of claim 11 wherein said effective amount is about 0.002 to about 3.4 g per kg of body weight per day.

13. The method of claim 11 wherein said effective amount is about 0.003 g to about 2.5 g per kg. of body weight per day.

14. The method claim 11 wherein the lauric acid is orally administered in a nutritional composition.

15. The method of claim 14 wherein said nutritional composition is nutritionally complete.

16. The method of claim 11 wherein said Helicobacter is *H. pylori*.

17. A nutritional composition comprising at least one monoglyceride of a $C_8$–$C_{16}$ fatty acid in an amount of about 0.05 g to about 10 g per 100 calories of composition.

18. The nutritional composition of claim 17 wherein the effective amount is about 0.1 g to about 8 g per 100 calories of composition.

19. The nutritional composition of claim 17 wherein the effective amount is about 0.2 g to about 6 g per 100 calories of composition.

20. The nutritional composition of claim 17 wherein the monoglyceride is a monoglyceride of a $C_9$–$C_{15}$ fatty acid.

21. The nutritional composition of claim 17 wherein the monoglyceride is a monoglyceride of a $C_8$–$C_{14}$ fatty acid.

22. The composition of claim 17 which further comprises about 0.5 g to about 10.0 g protein, about 0.1 g to about 9.0 g lipid, and about 6.0 g to about 25.0 g carbohydrate, said percentages being based on 100 calories of the composition.

23. The composition of claim 18 which further comprises about 0.5 g to about 10.0 g protein, about 0.1 g to about 9.0 g lipid, and about 6.0 g to about 25.0 g carbohydrate, said percentages being based on 100 calories of the composition.

24. The composition of claim 17 which further comprises about 1.0 g to about 8.0 g protein, about 0.2 g to about 8.0 g lipid, and about 7.0 g to about 22.0 g carbohydrate, said percentages being based on 100 calories of the composition.

25. The composition of claim 18 which further comprises about 1.0 g to about 8.0 g protein, about 0.2 g to about 8.0 g lipid, and about 7.0 g to about 22.0 g carbohydrate, said percentages being based on 100 calories of the composition.

26. The composition of claim 17 which further comprises about 1.8 g to about 6.2 g protein, about 0.4 g to about 7.0 g lipid, and about 8.0 g to about 20.0 g carbohydrate, said percentages being based on 100 calories of the composition.

27. The composition of claim 18 which further comprises about 1.8 g to about 6.2 g protein, about 0.4 g to about 7.0 g lipid, and about 8.0 g to about 20.0 g carbohydrate, said percentages being based on 100 calories of the composition.

28. The composition of claim 26 which further comprises vitamin and minerals.

29. The composition of claim 27 which further comprises vitamin and minerals.

30. The composition of claim 17 which is nutritionally complete.

31. A nutritional composition comprising lauric acid in an amount of about 0.05 g to about 10 g per 100 calories of composition.

32. The nutritional composition of claim 31 wherein the effective amount is about 0.1 g to about 8 g per 100 calories of composition.

33. The nutritional composition of claim 31 wherein the effective amount is about 0.2 g to about 6 g per 100 calories of composition.

34. The nutritional composition of claim 32 which further comprises about 0.5 g to about 10.0 g protein, about 0.1 g to about 9.0 g lipid, and about 6.0 g to about 25.0 g carbohydrate, said percentages being based on 100 calories of the composition.

35. The nutritional composition of claim 33 which further comprises about 0.5 g to about 10.0 g protein, about 0.1 g to about 9.0 g lipid, and about 6.0 g to about 25.0 g carbohydrate, said percentages being based on 100 calories of the composition.

* * * * *